US00PP33979P2

(12) United States Plant Patent
Gielis

(10) Patent No.: US PP33,979 P2
(45) Date of Patent: Mar. 1, 2022

(54) ***SEMPERVIVUM* PLANT NAMED 'BELSEMCOB2'**

(50) Latin Name: *Sempervivum arachnoideum*
Varietal Denomination: Belsemcob2

(71) Applicant: Belgicactus B.V.B.A., Westerlo (BE)

(72) Inventor: Jef Gielis, Westerlo (BE)

(73) Assignee: BELGICACTUS B.V.B.A., Westerlo (BE)

( * ) Notice: Subject to any disclaimer, the term of this patent is extended or adjusted under 35 U.S.C. 154(b) by 0 days.

(21) Appl. No.: 17/188,199

(22) Filed: Mar. 1, 2021

(51) Int. Cl.
*A01H 5/12* (2018.01)
*A01H 6/32* (2018.01)

(52) U.S. Cl.
USPC ..... Plt./263.1
CPC ..... *A01H 6/32* (2018.05)

(58) Field of Classification Search
USPC ..... Plt./263.1
CPC ..... A01H 5/02; A01H 5/12
See application file for complete search history.

*Primary Examiner* — Kent L Bell
(74) *Attorney, Agent, or Firm* — Penny J. Aguirre

(57) ABSTRACT

A new cultivar of *Sempervivum* plant named 'Belsemcob2' characterized by its compact, well-branched growth habit producing many rosettes, its strong root system, its suitability for outdoor growing habit all year round, and its leaf surface that is densely covered with very white cobweb pubescence in spring, summer and autumn.

3 Drawing Sheets

Botanical classification: *Sempervivum arachnoideum.*
Variety denomination: 'Belsemcob2'.

CROSS REFERENCE TO A RELATED APPLICATION

This application is related to a European plant breeders' rights application filed on Nov. 25, 2019, application No. 2019/3083. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Sempervivum arachnoideum* plant and referred to hereinafter by its cultivar name, 'Belsemcob2'. The new cultivar of *Sempervivum* is a hardy succulent perennial grown for use as a landscape and container plant.

The new cultivar resulted from a controlled breeding program conducted by the Inventor in Westerlo, Belgium. The Inventor made a cross in 2011 between unnamed and unpatented plants of *Sempervivum arachnoideum* in the Inventor's breeding program as both the female and male parents. 'Belsemcob2' was selected as a single unique plant in 2013 from the resulting seedlings of the above cross.

Asexual propagation of the new cultivar was first accomplished by the Inventor by cuttings in 2013 in Westerlo, Belgium. Asexual propagation by cuttings and offshoots has determined the characteristics to be stable and reproduced true to type in successive generations.

SUMMARY OF THE INVENTION

The following traits have been repeatedly observed and are determined to be the characteristics of the new cultivar.

These attributes in combination distinguish 'Belsemcob2' as a unique cultivar of *Sempervivum.*

1. 'Belsemcob2' exhibits a compact, well-branched growth habit producing many rosettes.
2. 'Belsemcob2' exhibits a strong root system.
3. 'Belsemcob2' exhibits a very suitable outdoor growing habit all year round.
4. 'Belsemcob2' exhibits a leaf surface that is densely covered with very white cobweb pubescence in spring, summer and autumn.

The parent plants both differ from 'Belsemcob2' in having white cobweb pubescence that is less bright white and remains white for less time, and in having a weaker root system. 'Belsemcob2' can be most closely compared to the *Sempervivum* cultivars 'Jubilee' (not patented) and 'White Christmas' (not patented). Both are similar to 'Belsemcob2' in having white cobweb pubescence. 'Jubilee' differs from 'Belsemcob2' in having cobweb pubescence that is much less white and in having a weaker root system. 'White Christmas' differs from 'Belsemcob2' in having cobweb pubescence that is much less white.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listing by Plantarium, Plantipp, Floral-Daily, Hortweek, KVBC, facebook, Greenity, Plantago, and Hortipoint.

BRIEF DESCRIPTION OF THE DRAWINGS

The accompanying color photographs illustrate the overall appearance and distinct characteristics of 1.5-year-old plants of the new *Sempervivum* as grown outdoors in 8.5-cm containers in Westerlo, Belgium.

The photograph in FIG. 1 provides a close-up view of the cobweb pubescence of 'Belsemcob2'.

Figure 1:
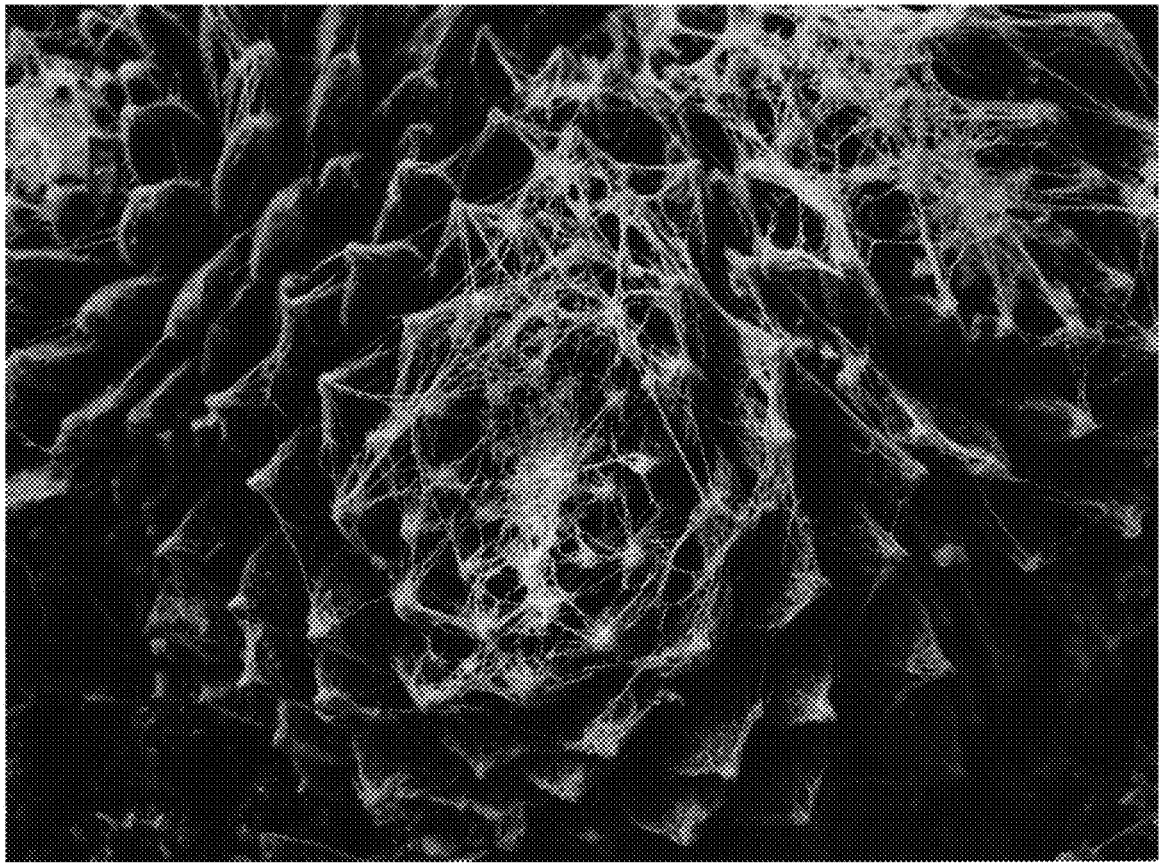
Figure 2:
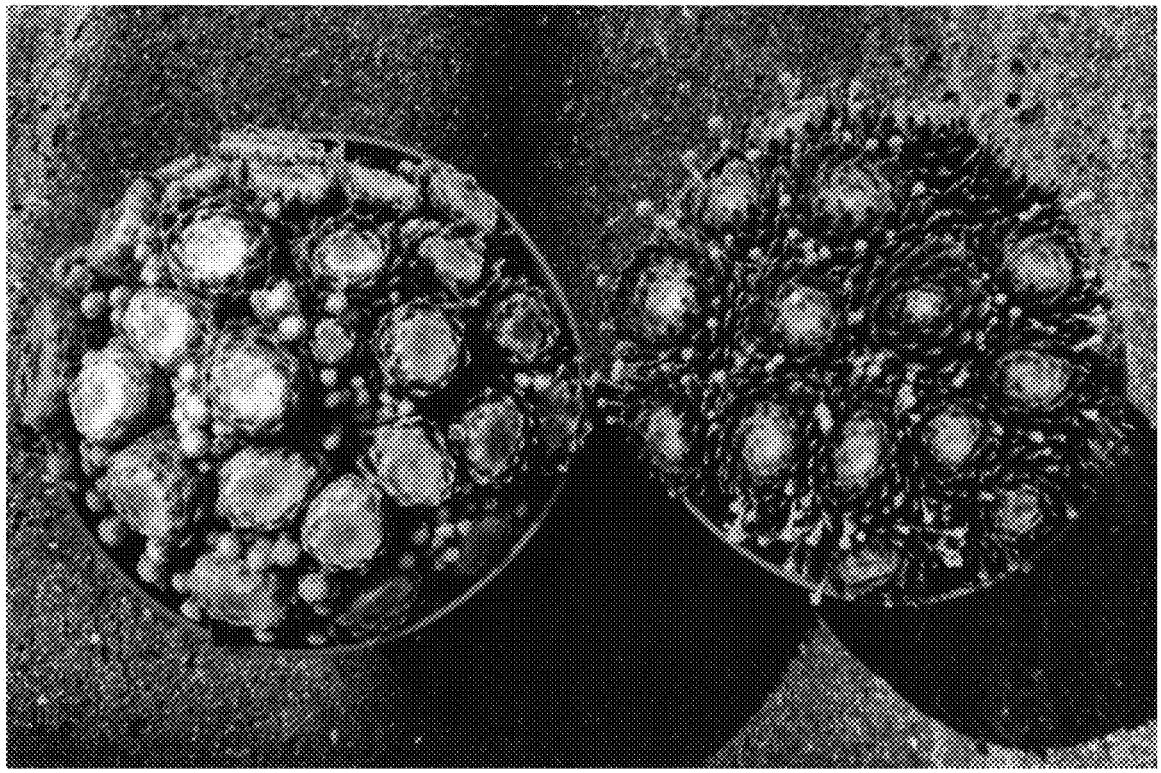

The photograph in FIG. 2 provides a comparison between a plant of 'Belsemcob2' (left) and a plant of 'Jubilee' (right).

Figure 3:
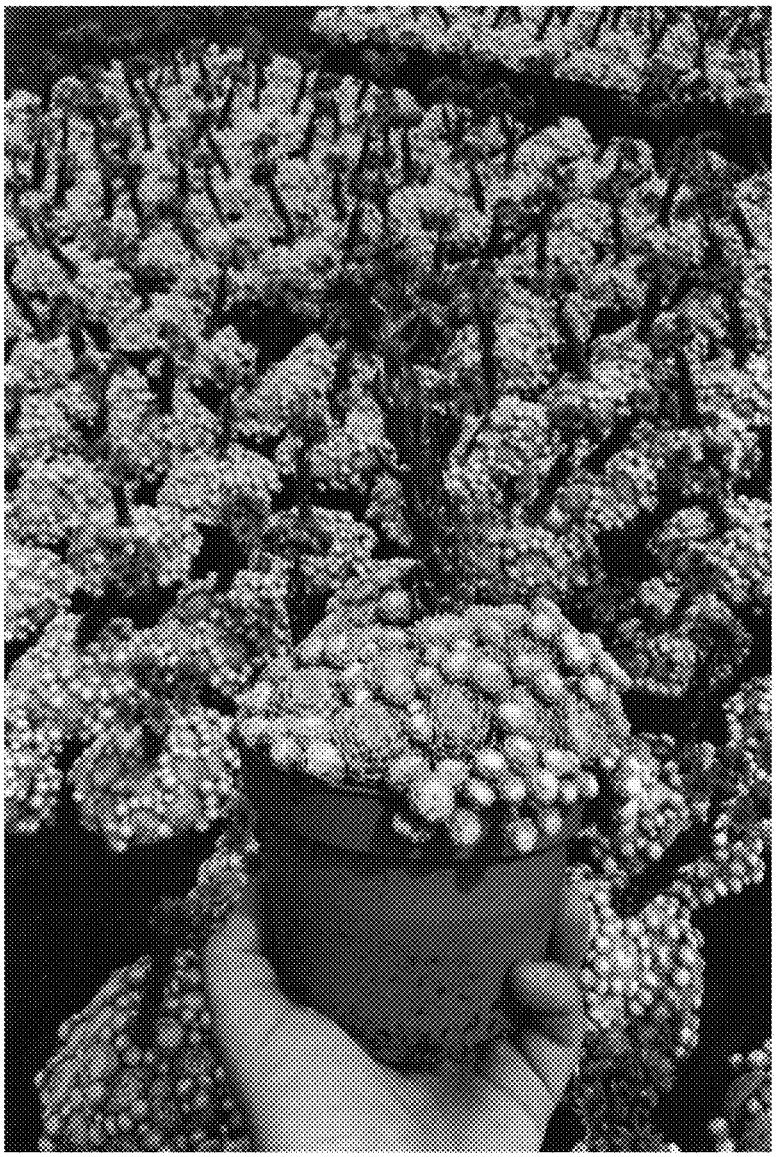

The photograph in FIG. 3 provides a close-up view of 'Belsemcob2' in bloom.

The colors in the photographs may differ slightly from the color values cited in the detailed botanical description, which accurately describe the colors of the new *Sempervivum*.

DETAILED BOTANICAL DESCRIPTION

The following is a detailed description of the new cultivar as observed on 1.5-year-old plants of the new *Sempervivum* as grown outdoors in 8.5-cm containers in Westerlo, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—April through August in Belgium (insignificant).

*Plant type.*—Evergreen succulent perennial.

*Plant habit.*—Basal rosette, offsets clustered around main rosette.

*Height and spread.*—Reaches up to 2.4 cm in height (without blooms) and 9 cm in spread (with off shoots), average diameter of main rosette is 2.8 cm.

*Hardiness.*—At least hardy in U.S.D.A. Zones 3 to 9.

*Diseases and pests.*—No susceptibility or resistance to diseases or pests has been observed; (*Sempervivums* are generally disease free unless grown under wet and cold conditions).

*Root description.*—Rhizomes grow from main rosette and hold offsets, rounded in shape, average of 2.5 cm in length and 1 mm in width, texture smooth, glabrous and matte, 155A, thinner roots 199C in color.

*Propagation.*—Cuttings and division of offsets.

*Root development.*—A cutting taken in July will fully root by September/October and will fill a P9 container by June.

*Growth rate.*—Moderate.

Stem description: Stemless.

Foliage description:

*Leaf shape.*—Oblong, succulent.

*Leaf division.*—Simple.

*Leaf arrangement.*—Rosette.

*Leaf base.*—Broad acute.

*Leaf apex.*—Abruptly apiculate.

*Leaf venation.*—No veins visible.

*Leaf margins.*—Ciliate and unlobed.

*Leaf attachment.*—Sessile.

*Leaf orientation.*—Slightly curved upward.

*Leaf substance.*—Succulent, average of 2 mm in thickness.

*Leaf number.*—An average of 75 per rosette and about 600 as grown in a 8.5 cm container.

*Leaf surface.*—Both surfaces are glaucescent, smooth, covered with short hairs, also on ciliate margins, tips and middle of the rosette are covered with thin cobweb type hairs, NN155A in color.

*Leaf color.*—Both surfaces young and mature 137A, base 145A, tips 199A.

*Leaf size.*—Average of 1.2 cm in length and 4 mm in width.

*Offshoots.*—Highly variable in size with leaf characteristics matching those of the main rosettes, stemless and arise from rhizomes, an average of 10 offshoots per plant in a 8.5 container based on being smaller than the main rosettes.

Flower description:

*Inflorescence type.*—Terminal cyme.

*Inflorescence quantity.*—One per plant.

*Inflorescence size.*—An average of 14 cm in height and 5 cm in diameter.

*Lastingness of inflorescence.*—At least one month, persistent.

*Flower shape.*—Stellate.

*Flower number.*—An average of 23 flowers per branched cyme.

*Flower fragrance.*—None.

*Flower buds.*—Spherical in shape, an average of 5 mm length and 3 mm in diameter, pubescent surface, color; 137C in color.

*Flower size.*—An average of 1 cm in height and 1.9 cm in diameter.

*Peduncles.*—Primary peduncle 11.5 cm in length, secondary peduncle 1.5 cm in length, both an average of 3 mm in width, both round, strong and flexible in strength with slightly pubescent surfaces, 137C in color.

*Pedicels.*—Round in shape, an average of 1 cm in length and 0.2 mm in diameter, 137C in color, strong and flexible in strength, slightly pubescent surface.

*Sepals.*—10, lanceolate in shape, entire margins, acute apex, truncate base, an average of 4 mm in length and 2 mm in width, color of inner and outer surfaces; 137C, tips 183A, both surfaces highly pubescent.

*Petals.*—10, rotate to upright, lanceolate in shape, acute base, acute apex, entire margins, about 3 mm in length and 1 cm in width, color; when opening and fully open 64D, when opening and fully open lower surface 56C, flushed with hints of 64D. both surfaces moderately pubescent with hairy margins.

Reproductive organs:

*Pistils.*—12, stigma; minute, less than 1 mm in length and 53C in color, style; an average of 6 mm in length, color; 53C, base 145A, ovary; none observed.

*Stamens.*—20, filament; up to 5 mm in length, 53A, base N155D, anther; 1 mm in length and width and 199C in color, pollen is low in quantity and too minimal for color determination.

*Fruit and seed.*—None produced.

It is claimed:

1. A new and distinct variety of *Sempervivum* plant named 'Belsemcob2' as described and illustrated herein.

* * * * *